(12) United States Patent
Buch-Rasmussen et al.

(10) Patent No.: US 6,562,011 B1
(45) Date of Patent: May 13, 2003

(54) MEDICATION DELIVERY DEVICE

(75) Inventors: Thomas Buch-Rasmussen, Gentofte (DK); Benny Munk, Hvidorre (DK); Jens Ulrik Poulsen, Virum (DK); Henrik Ljungreen, Ballerup (DK); Peter Møller Jensen, Hørsholm (DK); Jens Møller Jensen, Copenhagen (DK)

(73) Assignee: Novo Nordisk A/S, Bagsvaerd (DK)

( * ) Notice: Subject to any disclaimer, the term of this patent is extended or adjusted under 35 U.S.C. 154(b) by 0 days.

(21) Appl. No.: 09/348,536

(22) Filed: Jul. 7, 1999

Related U.S. Application Data

(60) Provisional application No. 60/098,702, filed on Sep. 1, 1998.

(30) Foreign Application Priority Data

| Jul. 8, 1998 | (DK) | 1998 00909 |
| Nov. 17, 1998 | (DK) | 1998 01500 |

(51) Int. Cl.$^7$ .............................................. A61M 5/00
(52) U.S. Cl. ......................................................... 604/232
(58) Field of Search ................................ 604/200–201, 604/228, 232–234

(56) References Cited

U.S. PATENT DOCUMENTS

| 4,597,753 A | * | 7/1986 | Turley | 604/61 |
| 4,865,591 A | * | 9/1989 | Sams | 604/186 |
| 4,936,833 A | | 6/1990 | Sams | |
| 4,973,318 A | | 11/1990 | Holm et al. | |
| 5,137,511 A | * | 8/1992 | Reynolds | 604/88 |
| 5,226,895 A | | 7/1993 | Harris | |
| 5,364,369 A | * | 11/1994 | Reynolds | 604/187 |
| 5,549,575 A | | 8/1996 | Giambattista et al. | |
| 5,554,125 A | * | 9/1996 | Reynolds | 604/187 |
| 5,688,251 A | | 11/1997 | Chanoch | |
| 6,146,361 A | * | 11/2000 | DiBiasi et al. | 604/232 |

FOREIGN PATENT DOCUMENTS

| EP | 0 688 571 | 12/1995 |
| WO | WO 94/21213 | 9/1994 |
| WO | WO 95/13842 | 5/1995 |
| WO | WO 96/02290 | 2/1996 |
| WO | WO 97/49620 | 12/1997 |

\* cited by examiner

*Primary Examiner*—Brian L. Casler
*Assistant Examiner*—Kevin C. Sirmons
(74) *Attorney, Agent, or Firm*—Marc A. Began, Esq.; Richard W. Bork, Esq.; Reza Green, Esq.

(57) ABSTRACT

The present invention relates to a medication delivery device comprising a cartridge assembly, a dosing assembly and optionally a needle assembly. The cartridge assembly comprises a cartridge having a stopper adapted to receive a plunger means. Furthermore, the cartridge assembly has one end sealed with a pierceable sealing, said end comprising coupling means for engaging a needle assembly, and another end comprising coupling means for engaging the dosing assembly. At least one of the coupling means of the cartridge assembly is unitarily moulded with the cartridge. The dosing assembly comprises a plunger means and has coupling means for engaging the cartridge assembly. The cartridge assembly and the dosing assembly are coupled together for delivering selected doses of medication. The cartridge is preferably moulded from a plastic material, such as a transparent material, and may be housed in a cartridge housing for protection of the cartridge. The coupling means may be selected from threaded locks, snap locks, hinged locks, or bajonet locks. The medication delivery device is especially suitable for delivering insulin, growth hormone or other medicines.

7 Claims, 2 Drawing Sheets

MEDICATION DELIVERY DEVICE

CROSS-REFERENCE TO RELATED APPLICATIONS

This application claims priority under 35 U.S.C. 119 of Danish application nos. PA 1998 00909 filed Jul. 8, 1998 and PA 1998 01500 filed Nov. 17, 1998, and U.S. provisional application No. 60/098,702 filed Sep. 1, 1998, the contents of which are fully incorporated herein by reference.

The present invention relates to a medication delivery device having a cartridge and a dosing assembly coupled together for delivering selected doses of medication, wherein at least one of the coupling means of the cartridge is unitarily moulded with the cartridge.

BACKGROUND

Some medication, such as insulin is self-administered. The typical diabetes patient will require injections of insulin several times during the day. The required insulin dose will vary from patient to patient, and will for each patient often also vary during the day. Each patient will often establish a regimen for the insulin administration adjusted to his or her insulin need as well as lifestyle. Medication delivery pens have been developed to facilitate the self-administration of medication, such as insulin.

One prior art medication delivery pen includes a pen body assembly comprising a medication cartridge and a plunger device. A needle assembly may be connected to the pen body assembly. The medication is delivered by moving or pressing a plunger in the direction of the needle assembly thereby delivering the medication. When the medication in the cartridge is exhausted the pen body assembly is discarded. Depending on the medication needs for each individual the medication in the cartridge will last for several days. During this period the needle assembly will often have to be replaced by a new assembly or new needle due to increasing bluntness of the needle making injections painful for the patient.

More recent developments have revealed medication delivery pens, wherein the cartridge holder assembly can be disassembled from the pen body assembly after the medication therein has been exhausted, discarded and replaced by a new medicine-containing cartridge assembly.

An example of this is shown in EP 0 688 571 disclosing a medication delivery pen having a reusable pen body assembly and a disposable cartridge assembly that are threadedly engageable with one another. The cartridge assembly comprises a cartridge, a cartridge housing, a cap between the distal end of the cartridge and the housing, securing the cartridge in the housing and being adapted for engagement with a needle assembly. Furthermore, the cartridge comprises a plunger within the cartridge. The reusable pen body assembly is coupled through a threaded coupling to the cartridge housing. Thus, the total number of parts comprising the prior art cartridge assembly is high.

It is an object of the present invention to provide a medication delivery device wherein the amount of parts of the cartridge is minimized.

SUMMARY OF THE INVENTION

Accordingly, the present invention relates to a medication delivery device comprising a cartridge assembly, a dosing assembly and optionally a needle assembly, said cartridge assembly having one end sealed with a pierceable sealing, said end of the cartridge assembly comprising coupling means for engaging a needle assembly, and another end comprising coupling means for engaging the dosing assembly, said cartridge assembly further comprising a cartridge wherein at least one of the coupling means of said cartridge assembly is unitarily moulded with the cartridge, the cartridge further comprising a stopper adapted to receive plunger means, and said dosing assembly comprising plunger means has coupling means for engaging the cartridge assembly, and said plunger means is adapted to engage the stopper of the cartridge when the dosing assembly is coupled to the cartridge.

The unitarily moulded coupling or coupling ensure that the coupling is not accidentally released from the cartridge during use and storage. Also, the above-described medication delivery device has fewer parts that the prior art devices because at least one coupling means is moulded unitarily with the cartridge. Thereby the costs involved in the production and assembling of the device are reduced, and the device is more economical, which is an important feature for a disposable device.

The medical delivering device may either be manufactured as a disposable device which is sold pre-filled with the insulin or it may appear as a durable medical delivering device so designed that it can receive disposable cartridges with insulin.

In a preferred embodiment the dosing assembly is reusable and the cartridge assembly is disposable, and accordingly, a second aspect of the present invention is a medication delivery device wherein the dosing assembly is releasably coupled to the cartridge assembly.

The medication delivery device is preferably constructed so as to ensure that the plunger means abuts on the stopper during use of the device, such as attaching and releasing the needle assembly. It is understood that the plunger means must disengage the stopper when the cartridge assembly is deliberately released from a reusable dosing assembly because the medication in the cartridge has been exhausted and the cartridge assembly is to be discarded. In this situation the plunger means is to be retracted to the dosing assembly before assembling the device with a new cartridge assembly.

Securing the abutment of the plunger means on the stopper during use of the medication delivery device, in particular when the needle assembly is coupled to and/or decoupled from the cartridge assembly, may be carried out by a variety of means. In a preferred embodiment the abutment is secured by preventing the cartridge assembly from being inadvertently released from the dosing assembly.

In particular, when the cartridge assembly is released from the dosing assembly through a movement including an axial movement, such as through a threaded coupling, it is preferred that the means for releasably coupling the needle assembly and the cartridge assembly together are such that the coupling and/or decoupling of the needle assembly cannot cause an axial movement of the cartridge assembly with respect to the dosing assembly. Thus, in that respect examples of the preferred couplings between the needle assembly and the cartridge assembly include releasable snap locks. Another preferred embodiment includes a safety on the coupling between the dosing assembly and the cartridge assembly, such as hinge on the coupling or a threaded coupling releasable only after exerting an axial pressure on the coupling.

A second aspect of the present invention is a cartridge assembly for use in a medication delivery device, said cartridge assembly having one end sealed with a pierceable sealing, said end of the cartridge assembly comprising coupling means for engaging a needle assembly, and another end comprising coupling means for engaging the dosing assembly, said cartridge assembly further comprising a cartridge wherein at least one of the coupling means of said cartridge assembly is unitarily moulded with the cartridge, said cartridge further comprising a stopper.

The cartridge assembly may further comprise a cartridge housing for protecting the cartridge in use. Furthermore, when the cartridge is moulded unitarily with one coupling means the cartridge housing may comprise the other coupling means. Accordingly, in one embodiment of the invention the housing of the cartridge assembly comprises coupling means for coupling the cartridge assembly to the dosing assembly, preferably the coupling means is moulded unitarily with the housing. The cartridge is arranged within the cartridge housing. The cartridge housing may be non-releasably attached to the cartridge, once the cartridge is arranged in the housing, whereby the housing is disposed with the cartridge. In another embodiment the housing is reusable and the cartridge is arranged releasably in the housing.

In a preferred embodiment all the coupling means of the cartridge assembly are unitarily moulded with the cartridge. Thereby, it is possible to construct the cartridge assembly without the housing providing a cartridge assembly with even fewer parts.

The coupling means of the cartridge assembly may be for any suitable coupling, preferably a releasable coupling. Examples of the coupling are snap locks, such as snap locks with guidewire and sideways snap locks, snap locks released through threads, bajonet locks, luer locks, hinged locks, threaded locks and any suitable combinations thereof.

The coupling means unitarily moulded with the cartridge are preferably external coupling means, such as an external threaded coupling.

In particular the coupling means for engaging to the dosing means may be an external threaded coupling.

The cartridge may be moulded from any material suitable for medical containers. The cartridge is preferably moulded from a plastic material, e.g. by injection moulding. A suitable choice of material allows the cartridge to be at least partly transparent, whereby the user can see whether content, such as liquid is left in the cartridge. In a preferred embodiment the cartridge is totally transparent giving the user a greater possibility of inspecting the content of the cartridge.

By using a plastic material as compared to the usual glass material a great advantage is achieved in the production lines. Normally a significant quantity of the produced glass cartridges will be spoiled in the lines due to breakage, however the loss is greatly reduced by the use of plastic cartridges. Furthermore, the risk of small loose glass particles in the cartridges have been eliminated.

Also, by moulding the coupling(s) unitarily with the cartridge a very precise coupling mechanism may be obtained, since no further steps are to be taken to attach coupling means to the cartridge.

The cartridge may be of any suitable form, such as a cylinder. The cylinder may be constructed with various combinations of circular or non-circular inner and outer cross-section. In another embodiment the cartridge may be box-shaped having essentially rectangular or triangular cross-section.

The stopper is in sliding fluid tight engagement in the cartridge. The stopper is preferably made of plastic and/or rubber material.

The flexibility of the cartridge wall is not critical, however if the cartridge is too flexible the function of the stopper may be impaired. Mostly, the cartridge is made of a material only slightly flexible to non-flexible.

In order to enforce and strengthen the cartridge wall the cartridge may be integrally moulded with reinforcements. Thereby, the necessity of a protective housing may be obviated. Furthermore, a scale may be integrally moulded with the cartridge wall providing the user with a measure for the medication used and left.

In a most preferred embodiment the cartridge assembly is comprised only of a cartridge being sealed in one end with a sealing, being unitarily moulded with all couplings means and comprising a stopper.

In a cylindrical cartridge the two couplings of the cartridge assembly are generally opposing each other having the same axis. However, the coupling for engaging with the dosing assembly being separate from coupling for engaging the needle assembly may be arranged so that their axis are in any angle with respect to each other, such as perpendicular, or even parallel, but not overlapping.

Another aspect of the present invention is a cartridge being at least partly filled with liquid medication, such as insulin.

In another embodiment the invention relates to a medication delivery device for transferring medication from the cartridge into a syringe with a needle. In this embodiment the coupling means for engaging the needle assembly may be replaced by coupling means for engaging the syringe, or coupling means for both may be provided. The coupling means may be a syringe holder, for example a cylinder coupled to the cartridge comprising a central bore for receiving the syringe. The syringe is coupled to the cartridge having the needle piercing the sealing. By activation of the dosing means the metered amount of medication is driven into the syringe. The syringe is then ready for injection after being removed from the cartridge.

DRAWINGS

DETAILED DESCRIPTION OF THE INVENTION

Figure 1:
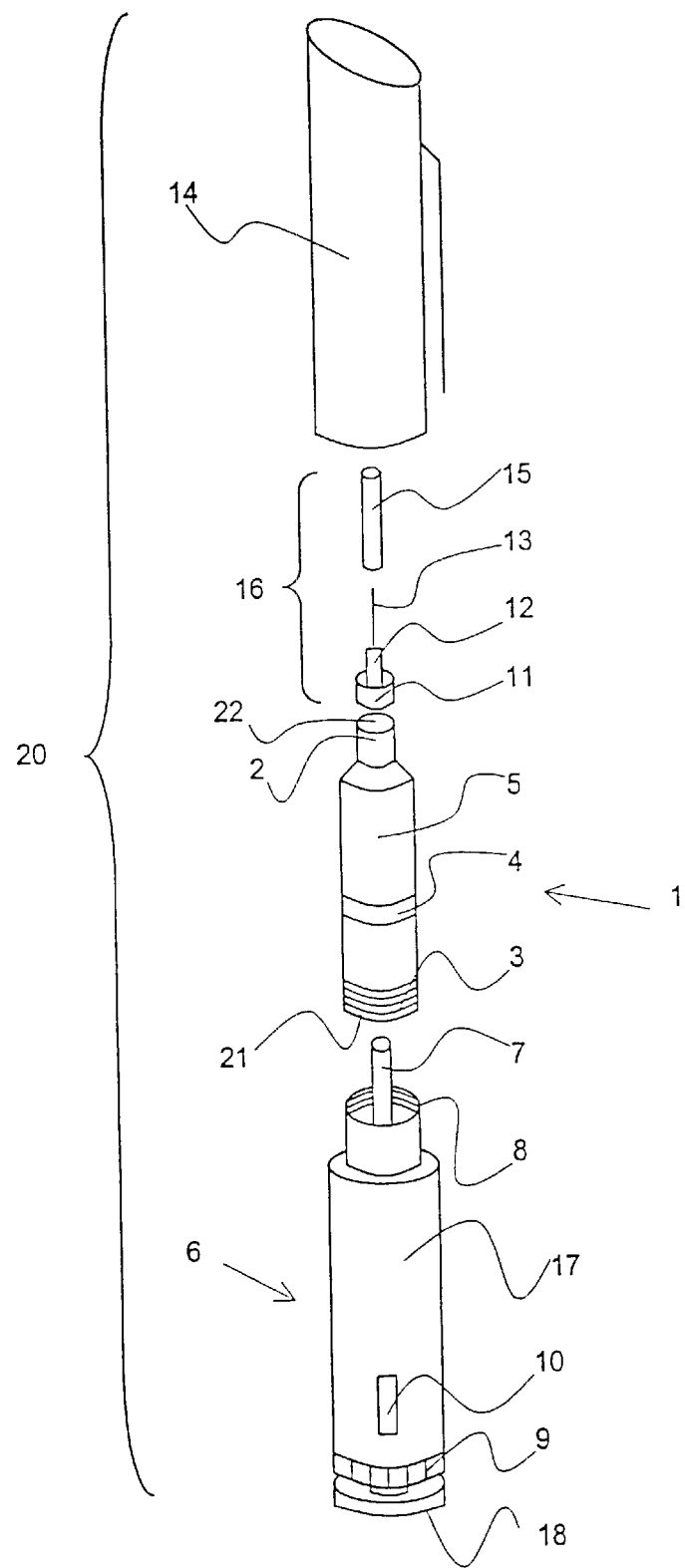
FIG. 1 is an exploded perspective view of the medication delivery device.
Figure 2A:
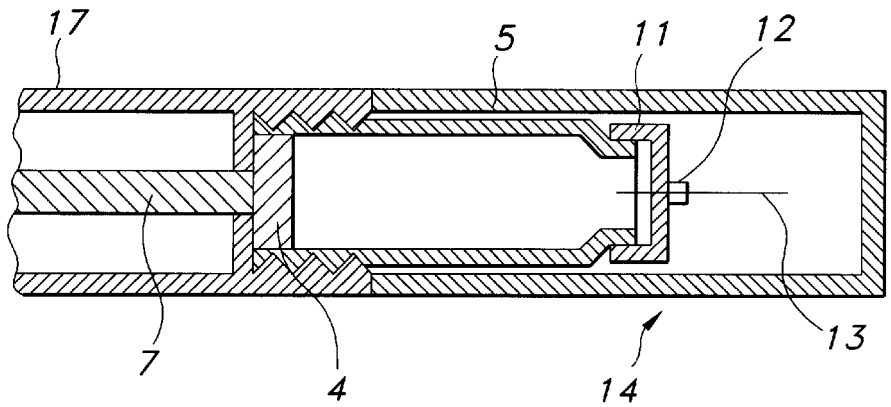
FIG. 2 is a cross-sectional view showing part of the medication delivery device, 2a immediately after assembling before the first injection, and 2b after some time of use.
Figure 2B:
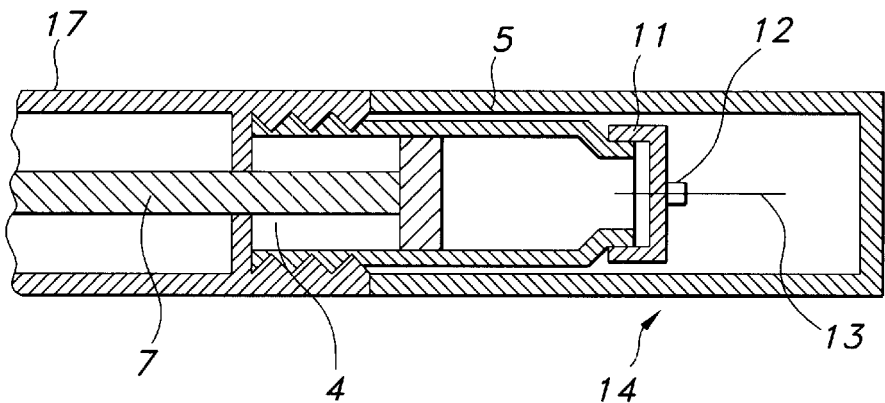

A medication delivery device in accordance with the present invention is identified generally by the numeral 20 in FIGS. 1 and 2. Medication delivery device 20 includes a dosing assembly 6, and cartridge assembly 1, a needle assembly 16 and a cap 14.

The dosing assembly 6 is illustrated in FIGS. 1 and 2. It is understood, however, that the dosing assembly 6 according to the invention may be any suitable dosing unit including plunger means, and accordingly, that variations from the depicted embodiment may be provided, and are considered to be within the scope of this invention. In the depicted embodiment the dosing assembly 6 includes a cylindrical housing surrounding the plunger means 17 of the dosing unit and having opposed proximal and distal ends.

In one aspect of the invention the plunger means comprises a rod element 7 which is adapted to engage the stopper 4 of the cartridge assembly 1. The rod element 7 advances axially into the cartridge 5 during injections. The dosing assembly may have any suitable driving means for advancing the rod element 7.

The dosing unit 6 preferably also comprises scale means 10 indicating the dosing quantity selected by activating the dose setting means 9 for defining specified selected doses of medication to be delivered. The selected dose may be delivered by actuating the actuator button 18. The actuator button is part of the driving means of the dosing assembly exerting its force on the rod element 7.

The dosing assembly further comprises coupling means 8 adapted for engagement with the cartridge assembly. The coupling means 8 may be internal or external couplings. In a preferred embodiment the coupling 8 is an internal coupling.

Figure 3:
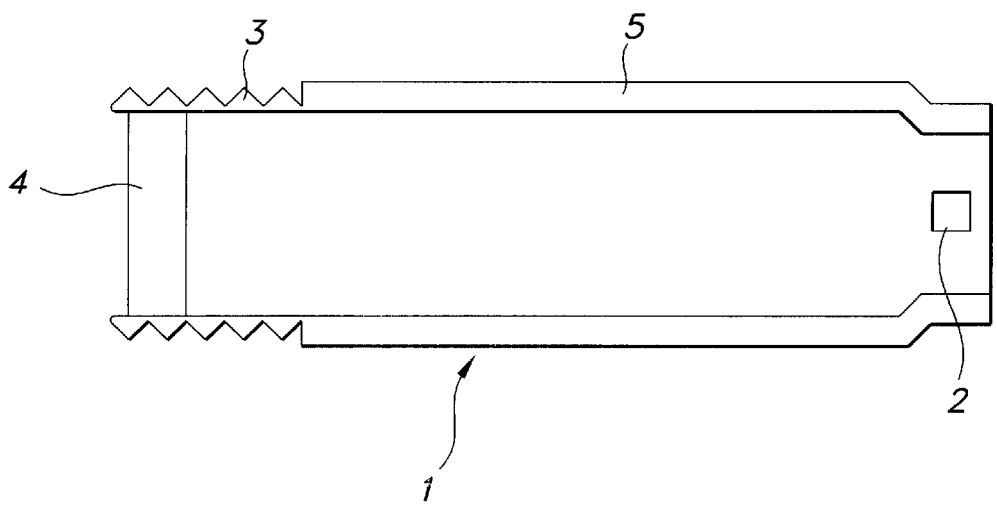
FIG. 3 is a cross-sectional view showing the cartridge before assembling of the medication delivery device.

The cartridge assembly 1 is illustrated in FIGS. 1 and 2, and in greater detail in FIG. 3. In FIG. 1 cartridge assembly 1 includes a moulded cartridge 5 extending from proximal end 21 to distal end 22.

At the distal end 22 of the cartridge assembly 1 is provided coupling means 2 for releasably mounting a needle assembly 11. At the proximal end 21 of the cartridge assembly 1 is provided coupling means 3 for mounting a dosing assembly 6. The coupling means are as described above.

Cartridge 5 also comprises a stopper 4 in sliding fluid tight engagement within said cartridge 5. The stopper 4 is adapted to receive the plunger means, such as a rod element 7 of the dosing assembly 6. The rod element 7 is adapted to exert an axial movement of the stopper 4 towards the sealed end 22 of the cartridge 5.

The cartridge assembly 1 may further comprise a housing for protecting some or all of the cartridge 5. When the cartridge assembly 1 includes a housing, one of the couplings 2, 3 of the cartridge may be moulded unitarily with the housing.

Instead of the protective housing the cartridge 5 may have integrally moulded reinforcements of the cartridge wall.

The depicted cartridge 5 is cylindrical having couplings 2, 3 at opposed ends. However, the cartridge may obtain any suitable form and the cross-section may be circular or non-circular, such as substantially triangular or oval.

The device according to the invention may include a protective cap 14 that is removably mounted over the cartridge assembly 1 and/or the needle 11 and which is removed before injection of the medication in the cartridge 5. The cap further ensures that the content of the cartridge is protected against sunlight.

Referring to FIG. 3 the coupling means of the cartridge are shown in greater detail. The coupling means 3 is an external thread, whereas the coupling means 2 is a recess for a snap lock of the needle assembly. Both coupling means are moulded unitarily with the cartridge.

The various parts of the medication delivery device are advantageously made of plastics, e.g. by injection moulding.

The medication delivery device 20 may further comprise any appropriate needle assembly 11, such as a double ended needle 13 having opposed proximal and distal points and a lumen extending axially therebetween.

A mounting hub 12 is engaged on the needle 13 and is removably connected to the coupling means 2 at the needle end of the cartridge assembly. The relative location of the mounting hub 12 ensures that the proximal point of the needle 13 will pierce the sealing when the mounting hub 12 is engaged with the coupling means 2 on the cartridge assembly 1.

The needle assembly 11 may further comprise a removable shield or cap 15 for protecting against accidental needle sticks.

The device according to the invention is suitable for delivering pre-set dosages of insulin, it is however understood that the device is suitable for the injection of pre-set dosages of other liquids.

In use the user will set the dose by means of the dose setting means 9. Before activating the actuator button 18 the cap 14 must be removed from the cartridge assembly 1 whereby the device 20 is prepared for an injection. The injection is effected by activating the actuator button 18, which again will cause the stopper 4 to be moved towards the sealed end 22 of the cartridge 5, thereby delivering the desired pre-set dosage. A subsequent dosage of medication will be set in exactly the same manner as described above. However, for such a subsequent dosage, the rod element 7 and the stopper 4 will be in a partly advanced position as starting point. Dose setting and injections can be carried out until all of the medication has been used.

What is claimed is:

1. A medication delivery device comprising a cartridge assembly having opposite ends and a dosing assembly for setting a desired dose and acting on the cartridge assembly to cause the desired dose to be delivered, wherein:

the cartridge assembly includes a molded cartridge and a stopper disposed in the cartridge, wherein one end of the cartridge assembly is sealed with a pierceable sealing, wherein the one end includes a first coupling means for releasably mounting a needle assembly having a skin-piercing needle, and wherein the other end of the cartridge assembly includes a second coupling means for engaging the dosing assembly, wherein at least one of the coupling means is unitarily molded with the cartridge, and wherein the dosing assembly includes a housing, a plunger, and a mechanism for setting a desired dose and for moving the plunger relative to the housing in an axial direction for administering a set dose, and wherein the dosing assembly housing includes a coupling member for engaging the second coupling means of the cartridge assembly for securing the housing against axial movement relative to the cartridge assembly such that the plunger engages the stopper for moving the stopper in response to the plunger movement wherein the at least one coupling means of the cartridge assembly is a threaded coupling and wherein the second coupling means is an external threaded coupling.

2. The medication delivery device according to claim 1, wherein both said coupling means of said cartridge assembly are unitarily molded with the cartridge.

3. The medication delivery device according to claim 1, wherein the said at least one coupling means of said cartridge assembly is an external coupling.

4. The medication delivery device according to claim 1, wherein the cartridge is molded of a plastic material.

5. The medication delivery device according to claim 4, wherein the cartridge is at least partly transparent.

6. The medication delivery device according to claim 1, wherein the dosing assembly further comprises a scale.

7. The medication delivery device according to claim 1, wherein the coupling means of the cartridge assembly are opposed.

* * * * *